United States Patent
Wang et al.

[19]

[11] Patent Number: 5,971,976
[45] Date of Patent: Oct. 26, 1999

[54] MOTION MINIMIZATION AND COMPENSATION SYSTEM FOR USE IN SURGICAL PROCEDURES

[75] Inventors: Yulun Wang, Goleta; Kenneth Grace, Carpinteria; Darrin R. Uecker; Sudipto Sur, both of Santa Barbara, all of Calif.

[73] Assignee: Computer Motion, Inc., Goleta, Calif.

[21] Appl. No.: 09/014,698

[22] Filed: Jan. 28, 1998

Related U.S. Application Data

[63] Continuation-in-part of application No. 08/603,543, Feb. 20, 1996, Pat. No. 5,762,458.

[51] Int. Cl.$^6$ .................................................. A61B 17/00
[52] U.S. Cl. .............................. 606/1; 606/130; 600/102; 600/595; 395/93
[58] Field of Search ........................... 606/1, 130; 901/9, 901/10; 600/101, 102, 587, 595; 128/897, 898; 395/80–82, 88, 90, 93

[56] References Cited

U.S. PATENT DOCUMENTS 5,676,673  10/1997  Ferre et al. .................................. 606/1
5,807,284   9/1998  Foxlin ...................................... 600/595
5,807,377   9/1998  Madhani et al. ............................. 606/1
5,876,325   3/1999  Mizuno et al. ........................... 600/102

*Primary Examiner*—Linda C. M. Dvorak
*Assistant Examiner*—Bryan K. Yarnell
*Attorney, Agent, or Firm*—Blakely Sokoloff Taylor & Zafman

[57] ABSTRACT

A system for maintaining a substantially fixed distance between a localized surface of the heart and the distal end of a surgical device for use in endoscopic surgical procedures. The system comprises a stabilizer for minimizing localized motion of the heart in attached communication with a sensor for sensing localized motion of the heart in a region proximal the stabilizer and a controller in electrical communication with the sensor for processing data indicative of the localized motion of the heart in a region proximal the stabilizer. The processor is in electrical communication with a controller for a robotic arm that holds an instrument for use in an endoscopic surgical procedure, said instrument having a proximal and distal end, and said robotic arm in electrical communication with the controller. The robotic arm repositions the instrument in response to signals received from said controller to maintain a substantially same relative configuration between the localized surface of the heart and the distal end of the instrument.

1 Claim, 6 Drawing Sheets

MOTION MINIMIZATION AND COMPENSATION SYSTEM FOR USE IN SURGICAL PROCEDURES

The present application is a continuation-in-part application of U.S. patent application Ser. No. 08/603,543 filed on Feb. 20, 1996, now U.S. Pat. No. 5,762,458.

BACKGROUND OF THE INVENTION

1. Field of the Invention

The present invention generally relates to surgical systems. More particularly, the present invention relates to a system and method for minimizing the effect of motion due to a heartbeat during the performance of minimally invasive endoscopic surgical procedures and more particularly endoscopic coronary artery bypass grafting surgery.

2. Description of Related Art

Blockage of a coronary artery may deprive the heart of the blood and oxygen required to sustain life. The blockage may be removed with medication or by an angioplasty. For severe blockage, a coronary artery bypass graft (CABG) is performed to bypass the blocked area of the artery. CABG procedures are typically performed by splitting the sternum and pulling open the chest cavity to provide access to the heart. An incision is made in the artery adjacent to the blocked area. The internal mammary artery (IMA) or some other arterial source of blood-flow may then be severed and attached to the artery at the point of incision The IMA bypasses the blocked area of the artery to again provide a full flow of blood to the heart.

Splitting the sternum and opening the chest cavity can create tremendous trauma on the patient. Additionally, the cracked sternum prolongs the recovery period of the patient. As such, there have been developed systems that enable minimally invasive CABG procedures. These systems utilize hand held tools and small incisions, on the order of 3–5 inches in length, to provide access to the thoracic region of a patient.

Such minimally invasive procedures are conducted by inserting surgical instruments through small incisions, on the order of inches in the skin of the patient. Manipulating such instruments can be awkward, particularly when suturing a graft to an artery. These systems utilize direct visualization of the surgical site. Such systems do not enable a completely endoscopic approach to the CABG procedure because of the need for direct visualization of the site. Additionally, such systems do not enable a fully endoscopic approach because of the incision size necessary to adequately manipulate the surgical instruments at the surgical site.

A fully endoscopic approach utilizes small holes to provide access to the thoracic cavity. Each of these holes is on the order of 3–15 mm in diameter. In order to perform a CABG procedure in a fully endoscopic fashion (i.e. using 3–10 mm holes) a robotic system must be used to filter hand tremors and scale motions made by the surgeon.

One of the greatest risks a patient faces during a CABG procedure, whether it be performed open, or in a minimally invasive fashion, is the use of cardiopulmonary bypass (CPB). It has been found that the use of CPB may result in short and long term memory loss, stroke, edema, and a host of other problems related to the use of such a system.

Systems that are currently being used to perform minimally invasive CABG procedures, and all known systems that enable a fully endoscopic approach to the CABG procedure employ CPB. The patient's heart is stopped and the blood-flow that would normally reach the heart is fed through a machine which oxygenates the blood and feeds it back into the patient's bloodstream. Once the patient has been placed on CPB, the bypass procedure is performed on the stilled heart.

It is heretofore unknown to perform a fully endoscopic CABG procedure on a beating heart. This is because there is no apparatus or method for minimizing or eliminating the effects of a heartbeat during the procedure.

It is essential that the heart remain still so as to enable minimally invasive endoscopic CABG procedures. More particularly, the sutures that must be emplaced on the arteries are on the order of between 1 and 4 millimeters. During a minimally invasive CABG procedure, movement of the heart makes it essentially impossible to perform the procedure. As such, CPB may be currently used in an endoscopic CABG procedure.

To minimize risk to the patient, and to minimize operating time, what is needed in the art is a system that replaces conventional CPB for use in endoscopic CABG procedures. Such a system may minimize the motion of the heart such that a patient's heart need not be completely stopped and the patient need not be placed on CPB. Such a system may be used in conjunction with a robotic system for endoscopic surgeries such as that referred to hereinabove wherein such a system will include apparatus for measuring and compensating for or correcting for heart motion.

SUMMARY OF THE INVENTION

The present invention is a system for maintaining a substantially fixed distance between a localized surface of the heart and the distal end of a surgical device for use in endoscopic surgical procedures, the system comprising:

A stabilizer for minimizing localized motion of the heart;

a sensor for sensing localized motion of the heart in a region proximal the stabilizer;

a controller in electrical communication with the sensor for processing data indicative of the localized motion of the heart in a region proximal the stabilizer;

a robotic arm for holding an instrument for use in an endoscopic surgical procedure, said instrument having a proximal and distal end, said robotic arm in electrical communication with the controller; and wherein said robotic arm repositions the instrument in response to signals received from said controller to maintain a substantially same relative configuration between the localized surface of the heart and the distal end of the instrument.

DETAILED DESCRIPTION OF THE INVENTION

Figure 1:
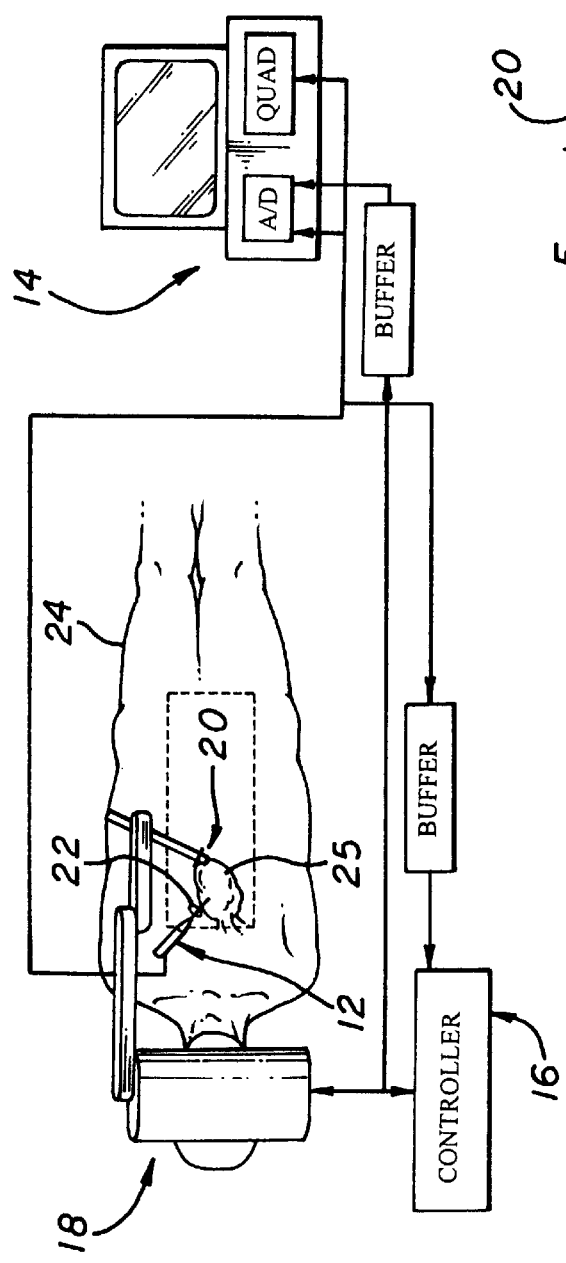
FIG. 1 is a diagram of a motion minimization and compensation system in accordance with the present invention.

Referring to the drawings more particularly by reference numbers, FIG. 1 shows a system 10 for reducing the effects of heartbeat, or other movement of an organ being operated upon in an endoscopic surgical procedures. For the purposes of the present application, the organ referenced will be the heart and the surgical procedure will be an endoscopic CABG procedure.

In the preferred embodiment, the system 10 may be used to minimize heart motion at a given location, sense and measure any residual motion in the area proximate the area where heart motion has been minimized, and control the movements of a robotic arm which holds an instrument to compensate for the residual reciprocating heart motion. In this way, endoscopic heart surgery may be performed without the use of Cardiopulmonary bypass.

The surgical instrument as well as the stabilizer each seat through apertures formed in a patient. Forming such apertures is well-known in the art of endoscopic surgery; however, it is believed that specific aperture placement provides advantages that have, until now, been unknown. The robotic system with which the present system 10 may be utilized is generally characterized and taught in U.S. patent application Ser. No. 08/603,543 filed on Feb. 20, 1996, which is now U.S. Pat. No. 5,762,458, and is incorporated herein by reference.

The system 10 generally includes a mechanical stabilizer 12, a coordinating processor 14, and a controller 16 for use with a robotic arm 18 having a surgical instrument 20 attached thereto, such as the robotic arm disclosed in the patent application incorporated herein by reference. The stabilizer 12 is configured to seat through a small aperture 22 in a patient 24 upon who's heart 25 a surgical procedure is to be performed. The aperture 22 is generally on the order of 3 mm–15 mm and may be formed by inserting a trocar into the patient 24. The use of trocars and similar devices are well known to create such apertures.

The aperture 22 should be formed in close proximity to the surgical site. As the present system 10 may be utilized in CABG and other coronary related procedures, the aperture 22 may be formed in intercostal spaces, spaces between the ribs. Alternatively, and to facilitate the performance of multiple by-pass procedures, apertures may be formed through or below the sternum, as pictured in FIGS. 7a and 7b. By accessing the thoracic cavity through the sternum, access is obtained to both the Left and Right Internal Mammary Arteries. Each of these may serve as a blood source to the heart. As depicted in FIG. 7b, apertures 23 may be formed towards the lower portion of the sternum and below the sternum to provide the appropriate access. At least one aperture 23 must be formed for the stabilizer 12 and one aperture formed for the surgical instrument 20. Of course more apertures may be formed for the inclusion of more surgical instruments.

Figure 3:
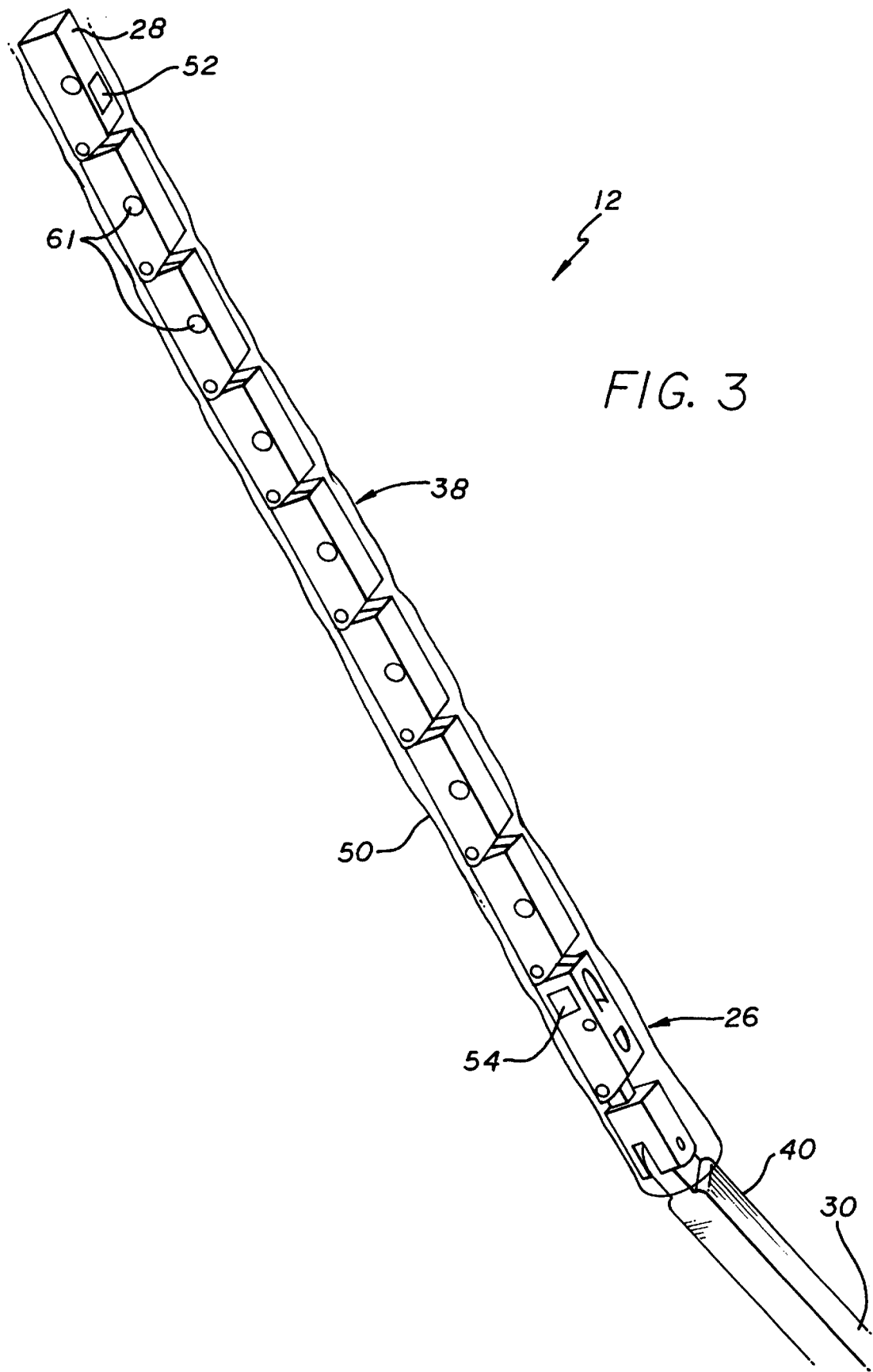
FIG. 3 is a perspective of an endoscopic stabilizer in a first configuration for use in the present invention.
Figure 4:
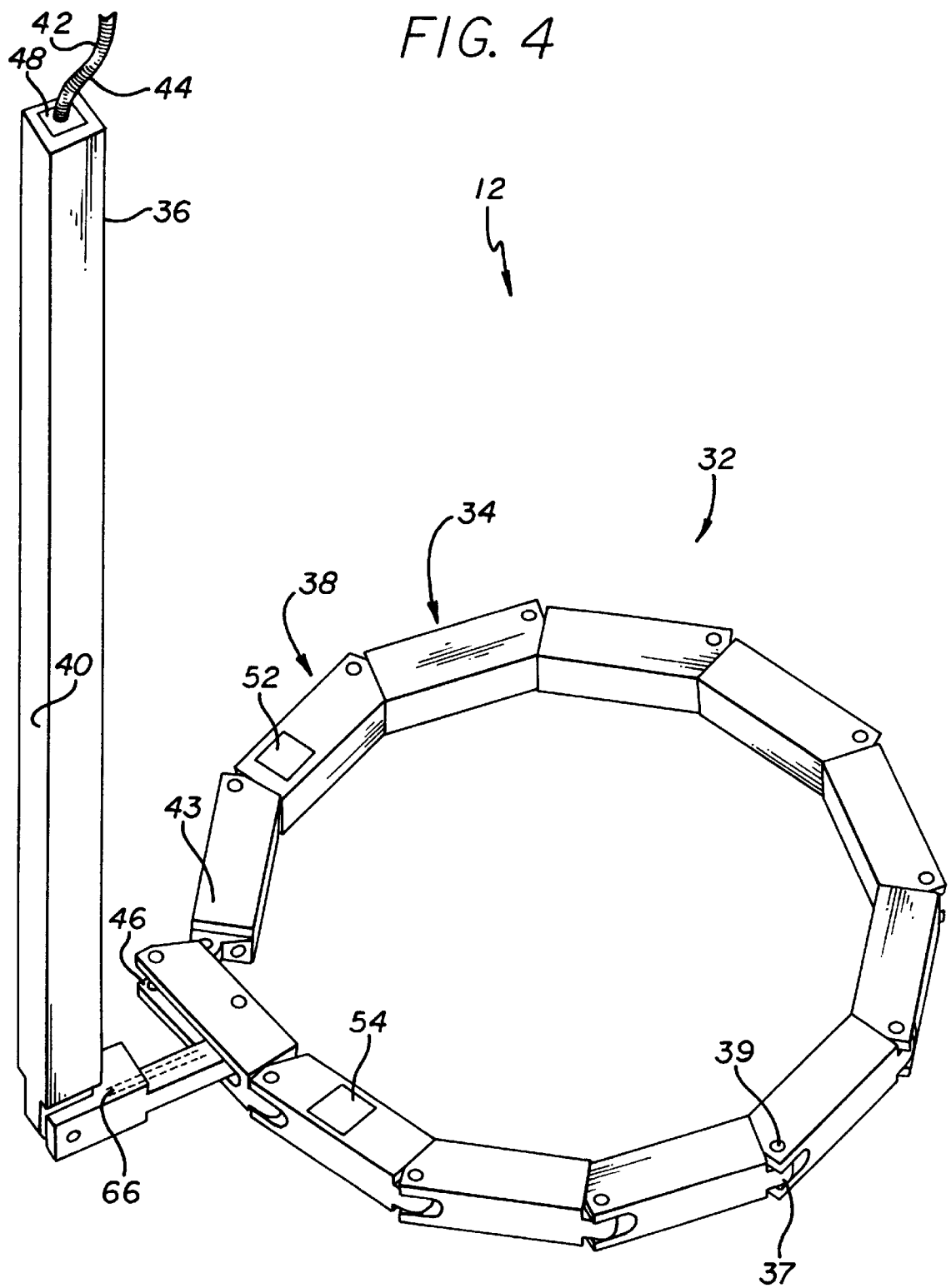
FIG. 4 is a perspective of an endoscopic stabilizer in a second configuration for use in the present invention.

The stabilizer 12 is depicted in more detail in FIGS. 3 and 4. As shown, the stabilizer 12 has two configurations. A first configuration 26 where the stabilizer 12 is substantially elongated having a distal end 28 and proximal end 30. The substantially elongated configuration 26 provides for insertion of the stabilizer 12 through a small aperture 22 such as those disclosed hereinabove.

The stabilizer 12 is preferably selectively configurable. In essence, the stabilizer 12 in accordance with the present invention must seat through the aperture 22 and additionally be useful in applying pressure to a local area of the surface of the heart 25 or other internal structure.

FIG. 4 sets out the second configuration 32 of the stabilizer 12. In this configuration of the stabilizer 12, the stabilizer 12 has a substantially circularly oriented distal portion 34 and an elongated proximal portion 36. To facilitate the reconfiguration of the stabilizer 12, it is preferably formed of a substantially rigid material, such as steel, and is comprised of a plurality of linkages 38. Each of the plurality of linkages 38 are pivotally attached to provide for pivotal planar motion and may be formed through the inclusion of joints 37 and pins 39 at each of the intersections of the plurality of linkages 38.

The length of the stabilizer 22 may be any length from 3 inches to 20 inches depending upon the use of the stabilizer 12 and the specific procedure for which it is to be used. The stabilizer does include one segment that may move in a plane perpendicular to the plane defined by the circularly oriented distal portion 34 of the second configuration 32. This linkage is known as the perpendicular linkage 40 and its use will be disclosed and taught hereinbelow.

The stabilizer 12 may be inserted into an aperture when in its first configuration 26, essentially elongated. Once the stabilizer has been inserted, a cable 42 serving as an actuation mechanism 44 may be pulled to reconfigure the linkages 38 into the second configuration 32. In this way the stabilizer 12 may be reconfigured to serve as a stabilizer without the necessity of a large opening within which it needs to be emplaced. The cable 42 extends along the entire length of the stabilizer and is attached at the distal end 28 thereof. When pulled, the cable 42 pulls the stabilizer 12 into the second configuration 32 pulling the distal end 28 into abutment with an adjacent one of the plurality of linkages 38.

To further effectuate the second configuration 32. The most distal linkage 43 of the stabilizer 34 may seat in a groove 46 formed in the perpendicular linkage 40. This ensures that the stabilizer 12 and its associated linkages 38 remain planar once the second configuration has been achieved. This can be further facilitated through the inclusion of a tensioning mechanism 48 disposed at the proximal end 36 of the stabilizer 12. Such a tensioning mechanism 48 keeps tension on the actuating mechanism and keeps the stabilizer in the second configuration 32 until the stabilizer is to be removed from the patient 24. The tensioning mechanism 48 may be a quick release spring biased latch that grasps the cable 42 and applies tension thereon until released by the user.

The stabilizer 12 may have a sheath 50 circumferentially surrounding it. The sheath may serve to aid in maintaining a sterile field. The sheath 50 may be formed of some easily steralizable flexible material such as surgical tubing, or other sterile flexible material well known to the skilled artisan.

The stabilizer 12 has disposed therein or thereon three inertial sensors 52. Such inertial sensors may be accelerometers, or micro-machined gyroscopes, both of which are well known devices and as such will not be discussed further herein. Each of the inertial sensors 52 independently measure the inertia of the stabilizer 12 resulting from any residual movement of the stabilizer 12 from movement of the structure against which it is pressed. In a CABG procedure, the residual movement would be due to movement of the heart 25.

By including three independent inertial sensors 52 measuring acceleration and/or inertia in planes orthogonal to each other, the relative position of a point on the stabilizer may be known. This is accomplished through known techniques including twice integrating the acceleration or inertia information and generating a vector representing the relative position of the stabilizer.

One drawback to the use of inertial sensors 52 such as the accelerometers disclosed hereinabove is that they tend to drift in their readings. To eliminate any error resulting from drift, an absolute position measuring device 54, such as the Minibird system produced by Ascension Technologies, or the Inside Track system produced by Polhemus may be included on the stabilizer 12 as well. The absolute position measuring device 54 is similar to a GPS system to provide the location of the absolute measuring device 54 with a resolution of approximately 0.2 mm. Because the precision of the system 10 must be better than 0.2 mm, the absolute position measuring device 54 may be used in conjunction with the inertia sensors 52 to provide very accurate and precise positional information with regard to the stabilizer 12. The inertia sensors 52 may be occasionally reset based upon position information provided by the absolute position device 54. Alternatively, or in conjunction with resetting the inertia sensors 52, filtering techniques for multi-sensor data fusion, such as Kalman Filtering or covariance intersection may be used.

The use of the inertia sensors 52 may not be necessary to provide the precise positional data required in the present system if the resolution of the absolute position measuring device can be made more precise. Such positioning systems do currently exist, however they are exceptionally expensive and as such have little applicability in the present system.

Alternatively, micro-machined gyroscopes or other inertial navigation systems (INS), such as those produced by Gyration corporation may be used in place of the inertial sensors 52 in conjunction with the aforementioned absolute position measuring device 54.

The inertia sensors 52 and the absolute position measuring device 54 may be permanently affixed to the stabilizer 12. This may be accomplished through the use of strong sterile adhesive. Alternatively, the sensors 52 and device 54 may be emplaced within the stabilizer 12 by hollowing out one or more of the plurality of segments 38 and emplacing the sensors therein. Data from each of the sensors may be delivered via wires or other well known means for transmitting electrical signals, such as radio or IR transmitters to the coordinating processor 14.

Figure 5:
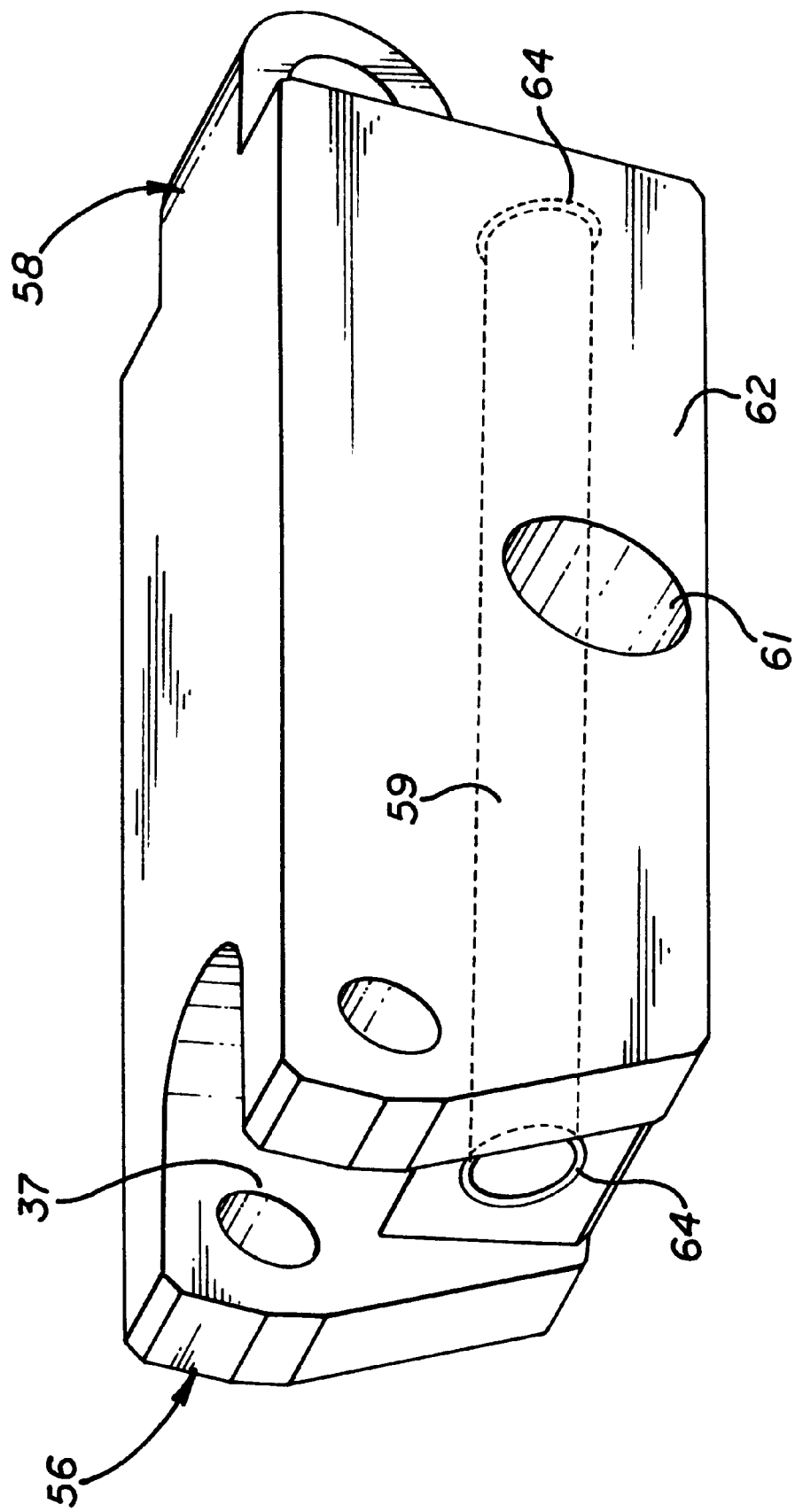
FIG. 5 is a perspective view of a segment of the stabilizer of FIGS. 3 and 4.
Figure 8A:
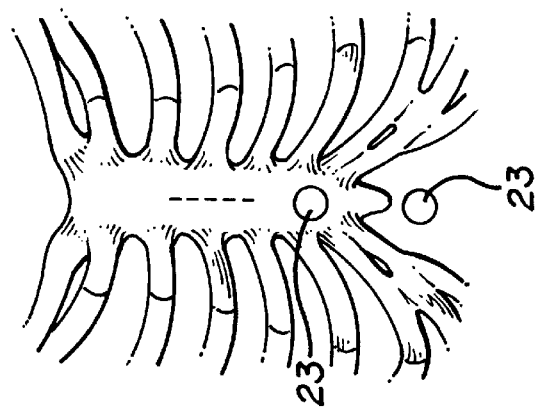
FIG. 8a is a diagram of the placement of ports for emplacing the various elements of a system in accordance with the present invention.
Figure 8B:
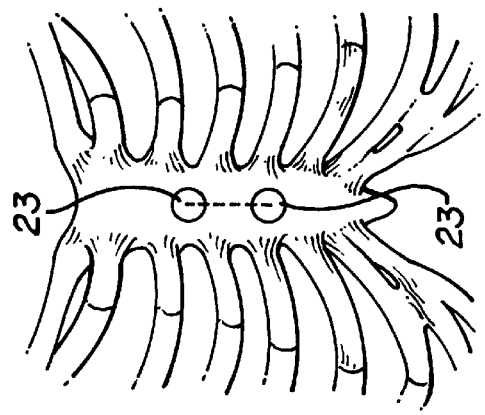
FIG. 8b is a diagram of the placement of ports for emplacing the various elements of a system in accordance with the present invention.

As shown in FIG. 5, each of the plurality of links 38 has a slot end 56 and a shoulder end 58 at the end opposite that of the slot end 56. Corresponding slot ends 56 and shoulder ends 58 interdigitate to provide for the construction of the stabilizer 12 in accordance with the present invention. Additionally, a channel 59 extends along the length 60 of each of the plurality of segments 38. The channel 59 is in communication with an aperture 61 formed in the bottom face 62 of each segment. The bottom face is the surface of each of the plurality of links that engages the organ, such as the heart.

Where the channel 59 terminates at the slot end 56 and shoulder end 58 of each link 38 an o-ring 64 is disposed to effectuate sealing between the channel 62 of each segment 38. Each segment 38 is configured so that when the stabilizer 12 is in the second configuration 32, each channel 62 is in sealed communication with an adjacent channel 632 thus providing a pathway through the stabilizer 12. A channel 66 in communication with the channel 62 that runs through each segment 38 extends through the perpendicular linkage 40 and terminates at the proximal end of the stabilizer 12. This channel may be connected to a suction device to create a vacuum that communicates through the apertures 61 in the bottom face of each segment 38. In this way, the stabilizer 12 may use suction to attach to the organ (heart) actually pull on the organ to stabilize the organ as opposed to using pressure on the organ to stabilize it.

Figure 6:
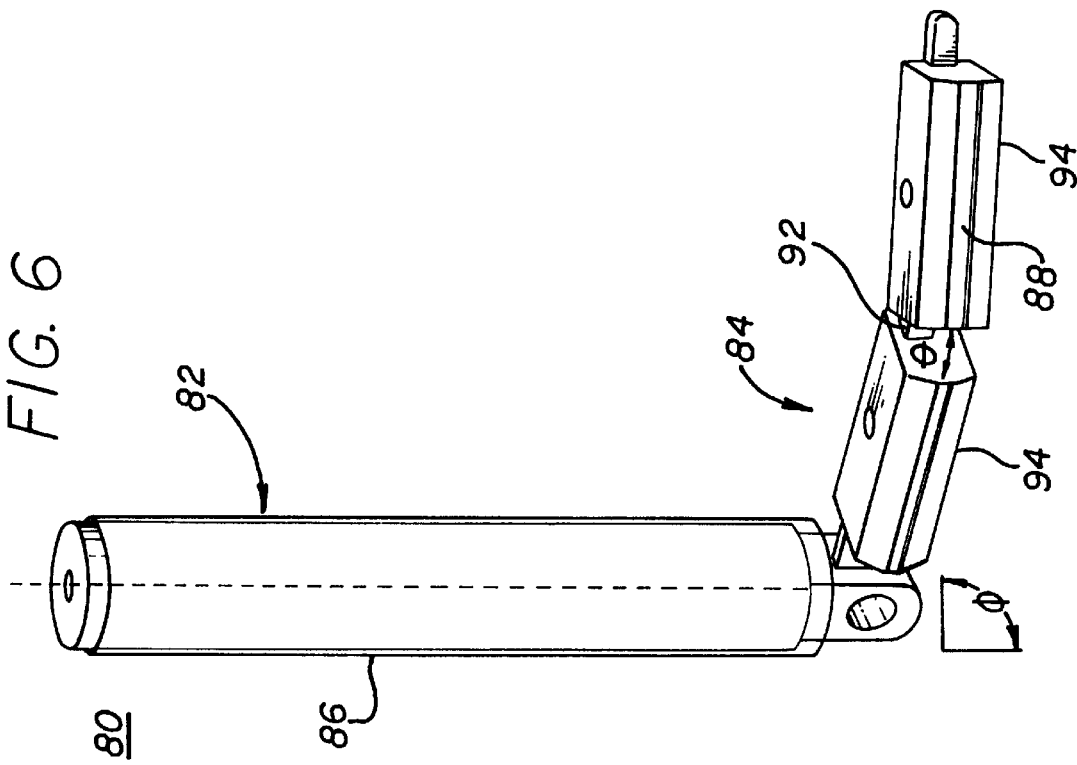
FIG. 6 is a perspective view of a stabilizer in accordance with the present invention.

Alternatively, a stabilizer 80 such as that depicted in FIG. 6 may be used in accordance with the present invention It is to be appreciated that the stabilizer 80 comprises a substantially rigid elongated proximal section 82 and a spring biased distal section 84. The stabilizer seats through a sheath 86 such that as the distal section of the stabilizer 80 emerges from the sheath 86 a first segment 88 moves an angle theta with respect to a second segment 90 to which it is pivotally attached via a hinge mechanism 92. As the second segment 90 emerges from the sheath 86, it moves an angle Phi with respect to the longitudinal axis X of the sheath 86.

The stabilizer 80 may include the channels that is disclosed with respect to the stabilizer 12 as well as the apertures in the bottom face portion 94 of each segment to effectuate a suction between the stabilizer 80 and the heart 25 or other organ which is to be stabilized.

Figure 7:
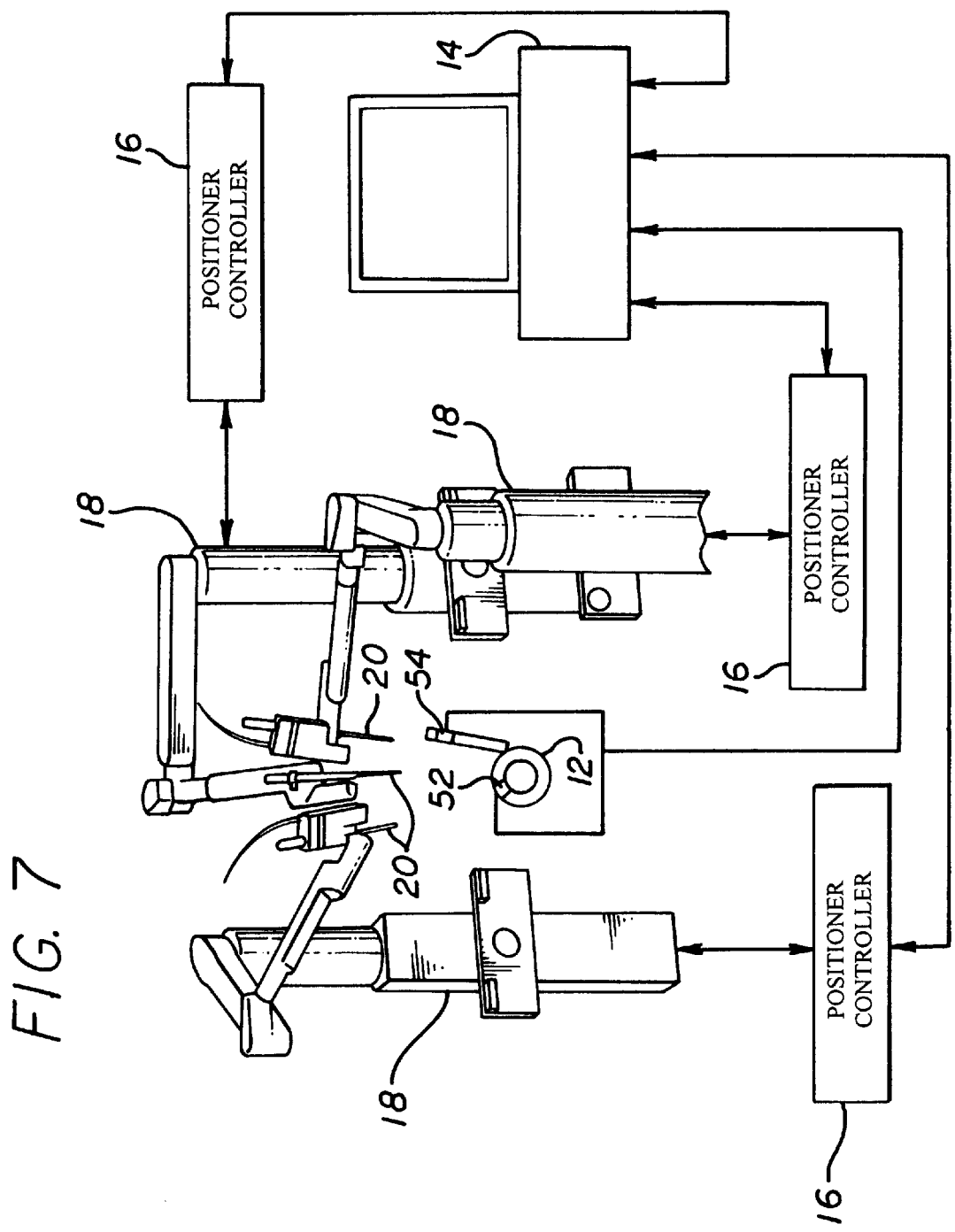
FIG. 7 is a diagram of a system in accordance with the present invention.

As shown in FIG. 7, the sensors 53, 54 are in electrical communication with the coordinating processor 14. The coordinating processor may be a personal computer, or it may be a processor specially designed to handle only the processing requirements of the present system. The coordinating processor 14 receives signals indicative of the inertia at each of the accelerometers or inertial sensors 52. Additionally, the processor 14 receives information from the absolute position measuring device 54.

Data from the sensors 52 and device 54 is fed to a coordinating processor 14 where the signals are processed to provide positional information relating to the stabilizer 12. Positional information may be obtained from each of the inertia sensors 52 and from the absolute position measuring device 54 through well known techniques including integrating the inertia data, and combining the data from each of the inertia sensors 52 with the data from the absolute position device 54. Because such techniques are well known they will not be discussed further herein.

From the positional information from each of the inertial sensors 52 and from the absolute position measuring device 54, the position of the substantially circularly oriented distal portion 34 of the stabilizer 12 in its second configuration 32 may be known and compared to its position at an earlier time.

Measurements preferably are taken on the order of 4–100 times/second to enable the system 10 to respond quickly to motion taking place at an area proximate the stabilizer 12. Once the measurements are taken and relayed to the coordinating processor 14, and then processed, they are then transmitted to the position controller 16 of a robotic arm 18.

Figure 2:
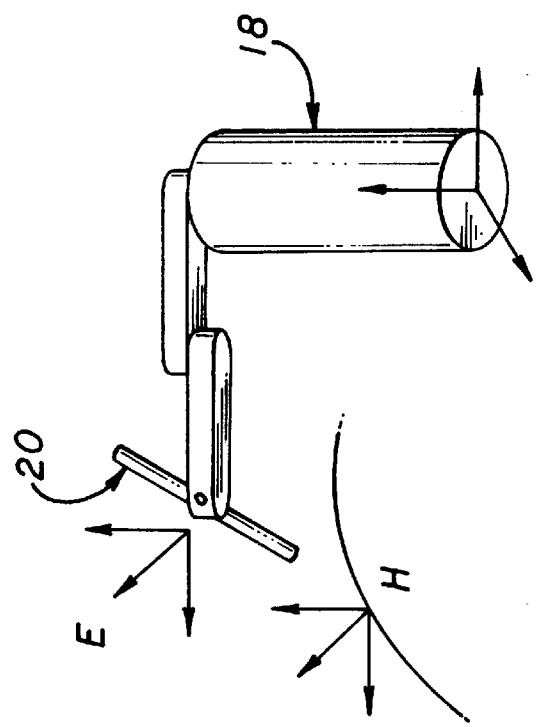
FIG. 2 is a perspective diagram depicting three frames of reference used in accordance with the present invention.

The task of processing the data relayed to the coordinating processor 14 also includes at least one coordinate frame transform. Essentially, and as depicted in FIG. 2, the motion measured at the heart H is not in the same coordinate frame as the required motion that must take place at the end of the surgical instrument 20 attached to the robotic arm 18. As such, a coordinate frame transform must be made from the coordinate frame at the heart H to the coordinate frame at the end of the robotic arm E, as the controller is programmed with the relationship between the end of the arm, and the end of a surgical instrument and the base of the robot. This is disclosed in the herein incorporated patent application.

Such coordinate frame transforms from one frame of reference to another are known in the art and as such will not be discussed in more detail herein. It is to be appreciated that several coordinate frame transforms are specifically set out in the patent application which is incorporated herein by reference as stated hereinabove.

To enable a proper coordinate frame transfer, the coordinating processor 14 must have an initial known positional relationship between the stabilizer 12 and the robotic arm 18. One way to accomplish such is to touch the stabilizer to the robotic arm 18 and have the processor store this position as the initial position. In this way, when the stabilizer is inserted into the patient 24, the coordinating processor 14 knows the relationship between the coordinate frame of the stabilizer and the coordinate frame and the arm of the robot 18.

The controller 16 and the robotic arm are fully disclosed and taught in the patent application included herein by reference. Information provided by the coordinating processor 14 is used to reposition a surgical instrument 20 disposed at the end thereof by providing positional data to the controller 16. The controller 16 receives the positional data, indicative of a new position for the robotic arm and transmits codes to actuators in the arm to move the robotic arm 18 into a new configuration in accordance with the motions measured at the coordinate frame H at the surface of the anatomical structure, such as the heart.

There may be supplied a plurality of robotic arms 18 each of which is in electrical communication with a separate controller 16. Each controller 16 receives information from the processor 14 and adjusts the position on the respective robotic arm 18 accordingly. In use with the present invention, each robotic arm 18 repositions an instrument, such as an endoscope, cutters, needle holders, TMR laser, scissors or other known endoscopic instrument in accordance with information provided from the processor 14. For example, if the stabilizer 12 moves in a direction towards the instrument, the respective robot will move the instrument 20 away from the stabilizer an amount of distance substantially equal to the distance and in the direction measured by the inertial sensors 52 and the ascension sensor 54. In this way, the relative distance and position between the end of the surgical instrument 20 and the surface of the anatomical structure being operated upon remains substantially fixed.

This is especially useful when the surgical instrument is an endoscope. Because the relative distance and angle is kept substantially the same, even if the anatomical structure is moving, such as a beating heart, it appears still to the surgeon. Coupled with one or more instruments that are additionally tied to the motion of the anatomical structure, surgery may be performed through small apertures on moving structures. This provides an great advantage over surgeries that are currently performed in that CPB is not necessary and a patient may still undergo a procedure in a minimally invasive fashion.

The motion of each robot 18 may additionally be tied to a master handle as disclosed in the system disclosed in U.S. patent application Ser. No. 08/603,543 filed on Feb. 20, 1996, incorporated herein by reference. In this case, the motions at both the master handle and the stabilizer 12 are fed into the processor 14 and resulting movement information is relayed to the controller 16. The robot 18 moves the instrument 20 in response to such information. In this way, a surgeon may manipulate a surgical instrument that is following the motion of an anatomical structure although it appears to be still. This is the case when two robots are used, one for holding and positioning an endoscope and another for holding and positioning another surgical instrument.

Although the present invention is shown to include inertial sensors and absolute position sensing devices, the same may be accomplished through the use of an optical sensor and a light source. For example, by shining a laser on the surface of the heart or other organ it is possible to determine the motion of the heart and such measured motion may be then relayed to the coordinating processor 14.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A system for maintaining a substantially fixed distance between a localized surface of the heart and a surgical device having a distal end for use in endoscopic surgical procedures, the system comprising:

a stabilizer for minimizing localized motion of the heart;

a sensor for sensing localized motion of the heart in a region proximal the stabilizer;

a controller in electrical communication with the sensor for processing data indicative of the localized motion of the heart in a region proximal the stabilizer;

a robotic arm for holding an instrument for use in an endoscopic surgical procedure, said instrument having a proximal and distal end, said robotic arm in electrical communication with the controller; and wherein said robotic arm repositions the instrument in response to signals received from said controller to maintain a substantially fixed distance between the localized surface of the heart and the distal end of the instrument.

* * * * *